United States Patent [19]

Struszczyk et al.

[11] Patent Number: 5,554,445
[45] Date of Patent: Sep. 10, 1996

[54] METHOD FOR SEED ENCRUSTING

[75] Inventors: Henryk Struszczyk, Zgierz, Poland; Olli Kivekäs, Tampere, Finland

[73] Assignee: Novasso Oy, Finland

[21] Appl. No.: 374,766

[22] PCT Filed: Jul. 29, 1993

[86] PCT No.: PCT/FI93/00308

§ 371 Date: Mar. 17, 1995

§ 102(e) Date: Mar. 17, 1995

[87] PCT Pub. No.: WO94/03062

PCT Pub. Date: Feb. 17, 1994

[30] Foreign Application Priority Data

Jul. 29, 1992 [FI] Finland ............................. 923421

[51] Int. Cl.$^6$ ............................................... B05D 7/00
[52] U.S. Cl. ..................... 428/403; 427/212; 427/215; 427/220; 427/421; 427/218; 504/100
[58] Field of Search ............................. 427/215, 220, 427/421, 218, 212; 428/403; 504/100

[56] References Cited

U.S. PATENT DOCUMENTS

| | | | |
|---|---|---|---|
| 4,881,343 | 11/1989 | Sannan et al. | 47/57.6 |
| 4,964,894 | 10/1990 | Freepons | 71/88 |
| 5,104,437 | 4/1992 | Hadwiger | 71/77 |

FOREIGN PATENT DOCUMENTS

| | | |
|---|---|---|
| 0243695A3 | 4/1989 | European Pat. Off. . |
| WO89/01288 | 2/1989 | WIPO . |
| WO89/07395 | 8/1989 | WIPO . |
| WO91/00298 | 1/1991 | WIPO . |

OTHER PUBLICATIONS

Plant Growth Promoter, Patent Abstracts of Japan, vol. 12, No. 242, C–510, Abstract of JP, A, 63–333310 (IHARA CHEM IND CO LTD), 13 Feb. 1988.

Struszczyk, et al., Some New Applications of Chitosan n Agriculture, International Conference on Chitin and Chitosan, 4, 1988, Trondheim, pp. 733–742 (No Month).

Heidari, Seafood Waste: The Potential for Industrial Use, Kemia–Kemi, vol. 19, No. 3 (1992), pp. 256–258.

Rawls, Prospects Brighten for Converting Chiten Wastes to Valuable Products, Chemical & Engineering News, vol. 62, No. 20 (1984), pp. 42–45 No Month.

Primary Examiner—Shrive Beck
Assistant Examiner—David M. Maiorana
Attorney, Agent, or Firm—Pollock, Vande Sande & Priddy

[57] ABSTRACT

Microcrystalline chitosan is used in seed encrusting in the form of liquid dispersion containing 0.0001–10 wt. % of polymer characterized by average molecular weight not lower than 1000, water retention value ranging from 200 to 5000%, deacetylation degree not lower than 35%, particle size in the range of 0.1–100 μm and energy of hydrogen bonds in a form of film of 10–25 kJ/mol. The liquid dispersion is introduced by spraying or mixing with a content of polymer not lower than 0.01 wt. %, whereafter the excess of solvent is removed and polymer film covering the seed is formed.

20 Claims, No Drawings

METHOD FOR SEED ENCRUSTING

This invention relates to seed encrusting or encapsulation by a film coating.

One of the most important parameters that affect the quantity of crops is the optimal amount of plants on a given sown area unit and keeping this amount unchanged until harvest time. This results above all from the quality of the sowable material and the protection of this material from diseases and pests. The most profitable and effective method to protect the plant against diseases and pests is the seed dressing or coating applied before sowing. The dressed sowable material ensures the high percentage of germinated plants, the plants grow quickly and are healthy and uniform, which results in more effective crops. The efficiency of the seed dressing depends on the properly choosed chemicals for seed dressing, the dosage of seed dressing chemicals and the method of applications.

There are well-known dry, semi-dry and wet seed dressing, coating and encrusting methods. The well-known method of encrusting seeds consists of mixing of the seed dressing chemicals formulated with a liquid or solid products for encrusting and subsequent coating on the seed. A coating is obtained where, after drying, the dressing chemicals bind with the seed. The seed is coated with the dressing chemicals in a uniform and firm way, dosage is precise and dosage of the dressing chemicals is optimized. Also dusting during dressing, packing, transporting and sowing is avoided which increases the work safety. The encrusting preparations should be characterized by high adhesion and should form up a solid film on the seed surface that is water-permeable or swells in water as well as is capable of biodegrading. At the same time the use of an encrusting agent should reduce the dosage of dressing chemicals as well as their losses into the environment.

There is known a way of seed treatment described in the Polish patent No. 124871 that consists of coating of the seed with a water-insoluble and moisture-permeable film containing the encrusting preparations as well as the plant pesticides. The encrusting agent is composed of 3.5–22.5% w/v of synthetic resins and 67–87% w/v of organic solvents such as alcohol or acetone.

There is also known a process for the preparation of coated seed described in the U.S. Pat. No. 4,344,979 that consists of coating of the seed with a coating agent containing hydrophilic synthetic polymers having hydroxyl, carboxyl, ester or carbamyl groups with combination with a peroxide compound such as calcium peroxide or magnesium peroxide.

Object of the WO 85/01736 is a hygroscopic coating composition for seed that comprises finely divided polyacrylamide and finely divided polyacrylate in an intimate admixture.

There is well-known a water-absorbing resin manufacture for seed-coating described in Japanese Patent No A280041 made by suspension of the polymerizing aqueous solution of monomers, initiators and other, with a film forming monomer and oil soluble initiator added near the end. Preferred as a water absorbing resin are carboxyl or carboxylate groups containing vinyl monomers and as the film forming monomers styrene and acrylonitrile. The chemical dressings for seed are used finally with the above coating mixture. There is also known a film-forming seed coating liquid composition on the base of acrylic polymers described in European Patent Application No. 89104943.9-2112 characterized in that it consists a polyacrylonitrile or acrylonitrile copolymer partially hydrolyzed with a molar ratio of carboxyl to amide groups of 1:0.001–1:1 in 1–15% w/v aqueous solution of pH ranging from 6.0 to 8.0, containing also nutrient media and/or dressing chemicals such as pesticides, fungicides, insecticides and/or dyes.

There is also known a method for manufacture of modified seed dressing described in Polish patent No 144192, which is characterized in that the dressing chemicals, such as pesticides, fungicides or insecticides, are mixed with chitosan, especially in a form of acidic solution with concentration of 0.01–3 wt %, adhesive additives in a form of water soluble acrylic polymers and surfactans as the sulfonated phenols or polyoxides, whereafter the modified seed dressing is used for coating of seed. The chitosan plays only a membrane creating agent role making the chemical dressing, such as pesticides, fungicides and insecticides, to stick on the seed surface.

The preparation of the known incrustating agents needs very expensive raw materials and toxic or inflammable solvents. Also the technological processes of preparation are very difficult. So there is no possibility to ensure that the final products would comply with the requirements concerning the preparations like this, i.e. high adhesion, creation of a polymer film with suitable resistance, permeability, biodegradation and non-phytotoxicity. At the same tine synthetic polymers not friendly to the environment and difficultly biodegradable are most frequently used in the encrusting preparations. The well-known encrusting preparations are only auxiliary agents for the chemical dressings protecting the seed during germination and at plant growing time. The well-known encrusting preparations create only films or membranes making the chemical dressing to stick onto the seed surface.

There is known from the manufacturer Siegfried Agro, Switzerland and the marketing company Suomen Farmipalvelu Oy, Finland a biologically decomposing, organic stimulator of the growth treatment preparations for seed on a base of standard chitosan containing 50% of this polymer in a solid, powder form. The method used for the seed treatment is connected with the wet or semi-dry systems pouring the powder into seed with the addition of suitable amount of water and mixing. This preparation is also recommended to be used together with chemical dressing such as pesticides, insecticides or fungicides. The well-known method of seed treatment is not distinguished by a suitable adhesion of the agent to the seed surface because the standard chitosan used in this method existing as a solid powder does not create a film form and it is joined on the seed surface only by weak physical bonds. Additionally, the encrusting process as well as storage, transport and sowing makes a lot of dust, losing an important part of the incrusting agent out from seed. The weak connection of the well-known encrusting agent to the seed also makes its easy washing out in the soil possible during rain or watering.

The object of this invention is a seed encrusting method by use of microcrystalline chitosan in a form of liquid dispersion to form a highly adhesive, permeable, biodegradable and bioactive film on the seed surface. The seed encrusting preparation consists of providing a uniform coating of the seed with a mixture of seed, encrusting agent and/or dyes and/or nutrient media that the preparation is optionally combined with.

In accordance with a preferred embodiment of the method of the invention the seed treatment by chitosan is characterized in that the microcrystalline chitosan in a form of liquid dispersion containing 0.0001–10 wt % of polymer characterized by average molecular weight not lower than 1000, preferably 10000–100000, water retention value ranging from 200 to 5000%, deacetylation degree not lower than 35%, particle size in a range of 0.1–100 μm and energy of hydrogen bonds of 10–25 kJ/mol, preferably 15–20 kJ/mol, is introduced on the seed, especially by spraying or mixing for 1–30 minutes, with a content not lower than 0.01 wt % of a dry polymer on the seed weight, preferably 0.02–0.1 wt %, and then the excess of solvent is removed and the seed covering film is formed. According to a preferred embodiment of the invention of the seed treatment by chitosan, the microcrystalline chitosan dispersion contains inorganic and/or organic volatile solvents such as water and/or alcohols or ketones, such as ethyl alcohol or acetone, as the liquid medium.

According to a preferred embodiment of the invention of the seed treatment by chitosan, the microcrystalline chitosan dispersion contains 0.001–0.1 wt % of dyes, on the weight of microcrystalline chitosan, added to the encrusting preparation to control the uniformity of the film coating the seed.

According to a preferred embodiment of the invention of the seed treatment by chitosan, the microcrystalline chitosan dispersion contains nutrients, such as nitrogen and/or phosphorus and/or potassium and/or microelements, in an amount up to 1.0 wt % on the weight of treated seed.

The method according to the invention allows to encrust the seed with microcrystalline chitosan in a form of dispersion to coat the seed surface by a highly adhesive film. The microcrystalline chitosan is a modern form of standard polymer, poly(2-amino-2-deoxy-β,D-glucose) originating mainly from shellfish wastes. Microcrystalline chitosan is characterized by several advantages, in comparison with standard chitosan, among other things high water retention value, biocompatibility, higher biodegradability, direct film-forming behaviour and bioactivity. An important object of the method according to the invention is to combine all the advantages of microcrystalline chitosan such as its biological behaviour including bioactivity such as antifungal, antipest, antidisease, or antivirus activity and controlled biodegradability with its direct film-forming behaviour. These properties of microcrystalline chitosan create a highly adhesive coating layer on the seed surface characterized by a suitable bioactivity, permeability to moisture and oxygen, as well as biodegradation with a controlled rate. The microcrystalline chitosan used in the method according to the invention is completely non-toxic to the seed, plants, animals and humans. The main advantage of the method according to the invention is the possibility to create a bioactive coating of seed without using the very toxic chemical dressings polluting the environment. At the same time microcrystalline chitosan according to the invention acts as a multifunctional agent for encrusting, coating and protecting of seeds including also reduction of nitrogen fertilizers consumption at the time of crop growing.

The method according to the invention eliminates also the use of all chemical pesticides from the dressing procedure as well as produces stronger and more vital plants with better utilization of nutrients from the soil. At the same time the method according to the invention needs only conventional existing equipment for encrusting and coating and increases the agricultural production at least 10% of total yield. The level of microcrystalline chitosan for the most effective result in the method according to the invention ranges from 20 g to 100 g of dry polymer on 100 kg of seed. In the application of the method according to the invention, the inorganic medium, such as water, and/or the volatile organic solvents, such as alcohols or ketones, such as ethyl alcohol and/or acetone, allow to cover the seed by a uniform polymeric film, creating a strong adhesive chitosan film on the seed surface.

Application of dyes in the method according to the invention supports the uniform film manufacture. At the same time the method according to the invention utilizes optionally a suitable amount of nutrients that contain nitrogen and/or phosphorus and/or potassium and/or microelements, located near to the germinated seed to form better conditions for the growing plants. Two main methods for testing of the effectivity of the encrusted seed manufactured according to the invention were used as follows:

Determination of seed germination power: the test was carried out on small seeds using one layer of wet blotting paper as well as on the large seed between two layers of wet blotting paper. The termination was carried out at room temperature using the same amount of distilled water for each type of seed. The average result of determination was based on three parallel test data.

Determination of sprouted plant number: the test was carried out in greenhouse conditions at temperature of 20°–25° C. The tested seeds were sowed into soil desinfected by steam. The green plants and roots were investigated after 12 days after sowing by dry weight determination, and the average of plants tested was calculated.

The method according to the invention is characterized by a higher germination power of tested seed in comparison to the non-treated control seed. The wheat was characterized by about 7.5% higher germination power, pea about 3% and bean about 7%, in comparison to the non-treated seed germination power. At the same time the investigations show that the method according to the invention is distinguished by a higher sprouted plant number of the treated seed: 15% higher in the case of bean, 8.0% in the case of wheat and 12% in the case of rape, in comparison to the same parameter characterizing the non-treated seed.

The method according to the invention is used in the agriculture instead of the well-known methods required for the chemical dressings for the protection of seed before sowing. The invention is explained further in the following examples which do not restrict the scope of claims.

EXAMPLE 1

1.33 Parts by weight of microcrystalline chitosan aqueous dispersion containing 1.5 wt % of polymer characterized by average molecular weight of 78000, deacetylation degree of 72%, water retention value of 1240%, particle size of 10–20 μm and energy of hydrogen bonds in a film form of 21.3 kJ/mol was mixed with 100 parts by weight of bean seed for 5 minutes. Then the treated seed were dried at 30° C. for 15 minutes. The obtained film of microcrystalline chitosan on the seed surface was characterized by a very good adhesion. No residues of chitosan were observed after the treatment process.

The germination power test for the treated seed containing 0.02 wt % of microcrystalline chitosan showed 97.5% effectivity, whereas the non-treated control seed were characterized by 91.3% effectivity. The sprouted plant number test showed that the percentage of sprouted plants of the treated seeds was 91%, whereas the same parameter for the non-treated seeds was 79.5%. The treated seeds produced after 12 days an average green plant weight of 2.23 g as well as 0.07 g of roots per plant, whereas the non-treated seeds produced 2.22 g and 0.06 g respectively.

EXAMPLE 2

20 Parts by weight of microcrystalline chitosan aqueous dispersion containing 0.1 wt % of polymer characterized by average molecular weight of 6700, deacetylation degree of 75%, water retention value of 3890%, particle size of 0.1–15 µm and energy of hydrogen bonds in a film form of 18.3 kJ/mol were mixed with 100 parts by weight of wheat seed for 15 minutes. Then the treated seed were dried at 33° C. for 30 minutes. The obtained film from microcrystalline chitosan on the seed surface was characterized by excellent adhesion. No chitosan residues were observed after the treatment process.

The germination power test for the treated wheat seed, containing 0.02 wt % of microcrystalline chitosan, showed 87.7% effectivity, whereas the non-treated control seeds were characterized by 80.3% effectivity. The sprouted plant number test showed that the percentage of sprouted plants from the treated seeds was 83%, whereas the same parameter for the non-treated seeds was 75%. The treated seeds produced after 12 days an average green plant weight of 0.27 g as well as 0.03 g of roots, whereas the non-treated seeds produced the values 0.25 g and 0.02 g respectively.

EXAMPLE 3

50 Parts by weight of microcrystalline chitosan aqueous dispersion with the properties as in Example 2 were mixed with 100 parts by weight of wheat seed as in Example 2. The obtained film of microcrystalline chitosan on the seed surface was characterized by excellent adhesion. No chitosan residues were observed after the treatment process.

The germination power test for the treated wheat seeds containing 0.05 wt % of microcrystalline chitosan showed 85.3% effectivity, whereas the non-treated control seed were characterized by 80.3% effectivity. The sprouted plant number test showed that the percentage of sprouted plants from the treated seeds was 80.5%, whereas the same parameter for the non-treated control seed was 75%. The treated seeds produced after 12 days an average green plant weight of 0.25 g as well as 0.03 g of roots, whereas the non-treated seed produced 0.25 g and 0.02 g respectively.

EXAMPLE 4

2.17 Parts by weight of microcrystalline chitosan aqueous dispersion containing 0.92 wt % of polymer characterized by average molecular weight of 312000, deacetylation degree of 59%, water retention value of 745%, particle size of 25–50 µm and energy of hydrogen bonds in a film form of 12.3 kJ/mol were mixed with 100 parts by weight of pea seed for 20 minutes. Then the treated seed were dried at 29° C. for 20 minutes. The obtained film from microcrystalline chitosan covering the seed surface was characterized by a very good adhesion. No chitosan residues were observed after the treatment process.

The germination power test for treated pea seed containing 0.02 wt % of microcrystalline chitosan showed 97.5% effectivity, whereas the non-treated control seed were characterized by 94.5% effectivity. The sprouted plant number test showed that the percentage of sprouted plants from the treated pea seed was 86.5%, whereas the same parameter for the non-treated seeds was 87%. The treated seeds produced after 12 days the average green plant weight of 0.64 g as well as 0.09 g of roots, whereas the non-treated seeds produced 0.58 g and 0.08 g respectively.

EXAMPLE 5

13.3 Parts by weight of microcrystalline chitosan aqueous dispersion with the properties as in Example 1 were mixed with 100 parts by weight of bean seeds for 5 minutes. The treatment process as well as the film behaviour were the same as in Example 1.

The germination power test for the treated seeds containing 0.2 wt % of microcrystalline chitosan showed 99.3% effectivity, whereas the non-treated control seeds were characterized by 99% effectivity. The sprouted plant number test showed that the percentage of sprouted plants from the treated seeds was 95%, whereas the same parameter for the non-treated seed was 80%.

EXAMPLE 6

0.76 Parts by weight of microcrystalline chitosan aqueous dispersion containing 5.25 wt % of polymer characterized by average molecular weight of 56375, deacetylation degree of 69%, water retention value of 1030%, average size of particles of 20–40 µm and energy of hydrogen bonds in a film form of 19.0 kJ/mol was mixed with 3 parts by weight of ethyl alcohol and 0.01 wt % of green dye and next they were mixed with 100 parts by weight of rape seeds. The treatment process as well as the film behaviour were the same as in Example 1.

The germination power test for the treated seeds containing 0.04 wt % of microcrystalline chitosan showed 95.5% effectivity, the same as for the non-treated seeds. The sprouted plant number test showed that the percentage of sprouted plants from the treated seeds was 85.3%, whereas the same parameter for the non-treated seed was 73.3%. The treated seed produced after 12 days the average green plant weight of 0.125 g, whereas the non-treated seed produced the value 0.100 g respectively.

EXAMPLE 7

50 Parts by weight of microcrystalline chitosan dispersion in water, ethyl alcohol and acetone mixture with a ratio of 5:1:0.5, containing 0.01 wt % of polymer with the properties as in Example 1, were mixed with 100 parts by weight of pea seeds with 0.02 wt % of red dye as well as 0.2 wt % of $K_2O$, 0.02 wt % of $P_2O_5$, 0.01 wt % of N and 0.001 wt % of microelements. The treatment process as well as the film behaviour were the same as in Example 2.

The germination power test for the treated seeds containing 0.05 wt % of microcrystalline chitosan showed 97% effectivity, whereas the non-treated seeds were characterized by 94.5% effectivity. The treated seeds produced after 12 days the average green plant weight of 0.60 g and 0.10 g of roots, whereas the non-treated seeds produced 0.58 g and 0.08 g respectively.

We claim:

1. Method for seed encrusting which comprises spraying or mixing a liquid dispersion of microcrystalline chitosan containing 0.0001–10 wt. % of polymer having an average molecular weight not lower than 1000, a water retention value from 200 to 5000%, deacetylation degree not lower than 35%, particle size in the range of 0.1–100 µm and energy of hydrogen bonds in a form of film of 10–25 kJ/mol, on seed in an amount to provide a content of polymer not lower than 0.01 wt. % based on the seed weight; and then removing excess solvent to thereby form a polymer film covering said seed.

2. A method as claimed in claim 1, characterized in that the microcrystalline chitosan dispersion contains inorganic and/or organic volatile solvents, such as water and/or alcohols or ketones.

3. A method as claimed in claim 1, characterized in that the microcrystalline chitosan dispersion contains 0.001–0.1 wt % of dyes, on the weight of microcrystalline chitosan, added to the incrustating preparation to control the uniformity of seed coating.

4. A method as claimed in claim 1, characterized in that the microcrystalline chitosan dispersion contains nutrients, such as nitrogen and/or phosphorus and/or potassium and/or microelements.

5. A method as claimed in claim 2, characterized in that the microcrystalline chitosan dispersion contains 0.001–0.1 wt % of dyes, on the weight of microcrystalline chitosan, added to the incrustating preparation to control the uniformity of seed coating.

6. A method as claimed in claim 2, characterized in that the microcrystalline chitosan dispersion contains nutrients.

7. A method as claimed in claim 6 wherein said nutrients are selected from the group consisting of nitrogen, phosphorous and microelements and mixtures thereof.

8. A method as claimed in claim 6 wherein said nutrients are in an amount up to 1.0 wt % on the weight of the treated seed.

9. A method as claimed in claim 3, characterized in that the microcrystalline chitosan dispersion contains nutrients.

10. A method as claimed in claim 9 wherein said nutrients are selected from the group consisting of nitrogen, phosphorous and microelements and mixtures thereof.

11. A method as claimed in claim 9 wherein said nutrients are in an amount up to 1.0 wt % on the weight of the treated seed.

12. The method of claim 1 wherein said polymer has an average molecular weight of 10,000–100,000.

13. The method of claim 1 wherein said polymer has an energy of hydrogen bonds in a form of film of 10–20 kJ/mol.

14. The method of claim 1 wherein said content of polymer is 0.02–0.1 wt. %.

15. The method of claim 2 wherein said liquid medium is selected from the group consisting of water, ethyl alcohol and acetone.

16. The method of claim 4 wherein said nutrients are selected from the group consisting of nitrogen, phosphorous and mixtures thereof.

17. The method of claim 16 wherein said nutrients are in an amount up to 1.0 wt. % based on the weight of the treated seed.

18. The method of claim 1 wherein said mixing of spraying is for 1–30 minutes.

19. An encrusted seed obtained by the method of claim 1.

20. A seed encrusted with a polymer film obtained from a dispersion of microcrystalline chitosan containing 0.0001–10 wt. % of a polymer having an average molecular weight not lower than 1000, water retention value ranging from 200 to 5000%, deacetylation degree not lower than 35%, particle size in the range of 0.1–100 µm and energy of hydrogen bonds in a form of film of 10–25 kJ/mol and wherein the content of polymer is not lower than 0.01 wt. % based on the seed weight.

* * * * *